United States Patent
Xu et al.

(10) Patent No.: US 11,727,669 B1
(45) Date of Patent: Aug. 15, 2023

(54) INTELLIGENT RECOGNITION METHOD OF HYPERSPECTRAL IMAGE OF PARASITES IN RAW FISH

(71) Applicant: Institute of Facility Agriculture, Guangdong Academy of Agricultural Science, Guangdong (CN)

(72) Inventors: Sai Xu, Guangdong (CN); Huazhong Lu, Guangdong (CN); Changyuan Zhang, Guangdong (CN); Xin Liang, Guangdong (CN); Guangjun Qiu, Guangdong (CN); Changxiang Fan, Guangdong (CN); Jian Peng, Guangdong (CN)

(73) Assignee: Institute of Facility Agriculture, Guangdong Academy of Agricultural Science, Guangzhou (CN)

( * ) Notice: Subject to any disclaimer, the term of this patent is extended or adjusted under 35 U.S.C. 154(b) by 0 days.

(21) Appl. No.: 18/050,478

(22) Filed: Oct. 28, 2022

(30) Foreign Application Priority Data

Mar. 17, 2022 (CN) .......................... 202210263992.1

(51) Int. Cl.
*G01N 33/12* (2006.01)
*G06V 10/28* (2022.01)
(Continued)

(52) U.S. Cl.
CPC ............. *G06V 10/58* (2022.01); *G01N 33/12* (2013.01); *G06V 10/28* (2022.01); *G06V 10/34* (2022.01);
(Continued)

(58) Field of Classification Search
None
See application file for complete search history.

(56) References Cited

U.S. PATENT DOCUMENTS

| 11,475,689 B2* | 10/2022 | Young | G06T 7/70 |
| 11,490,601 B2* | 11/2022 | Young | A01K 61/13 |

(Continued)

FOREIGN PATENT DOCUMENTS

| CN | 102890092 A | 1/2013 |
| CN | 103487380 A | 1/2014 |

(Continued)

OTHER PUBLICATIONS

Cheng et al., "Hyperspectral imaging as an effective tool for quality analysis and control of fish and other seafoods: Current research and potential applications," Trends in Food Science & Technology 37 (2014) 78-91 (Year: 2014).*

(Continued)

*Primary Examiner* — Soo Shin

(57) ABSTRACT

An intelligent recognition method of hyperspectral image of parasites in raw fish relates to optical detection technology, and includes step 1: obtaining a hyperspectral image of the raw fish in a wavelength range from 300 to 1100 nm; step 2: extracting a grayscale image of the hyperspectral image at a wavelength value of 437 nm, and obtaining a position range of fish meat in the grayscale image by performing a median filtering process and a binarization process on the grayscale image; step 3: extracting spectral signals of pixel points in the position range of the hyperspectral image, performing a first-order derivative process on the spectral signals, and import the spectral signals after the first-order derivative process into a preset first model, a second model, and a third model for analysis. The method can accurately distinguish the parasite body in the raw fish.

5 Claims, 3 Drawing Sheets

(51) Int. Cl.
*G06V 10/34* (2022.01)
*G06V 10/36* (2022.01)
*G06V 10/58* (2022.01)
*G06V 10/774* (2022.01)
*G06V 40/10* (2022.01)

(52) U.S. Cl.
CPC ............ *G06V 10/36* (2022.01); *G06V 10/774* (2022.01); *G06V 40/10* (2022.01)

(56) References Cited

U.S. PATENT DOCUMENTS

2008/0064058 A1   3/2008   Kapel et al.
2008/0199080 A1   8/2008   Subbiah et al.

FOREIGN PATENT DOCUMENTS

| CN | 111008970 A | 4/2020 |
| CN | 112204674 A | 1/2021 |
| JP | 2007286041 A | 11/2007 |

OTHER PUBLICATIONS

1st Office Action of counterpart Chinese Patent Application No. 202210263992.1 dated Apr. 24, 2022.
2nd Office Action of counterpart Chinese Patent Application No. 202210263992.1 dated May 18, 2022.
Notice of Allowance of counterpart Chinese Patent Application No. 202210263992.1 dated May 27, 2022.
Chengjing Cai et al., Research on Hyperspectral Remote Sensing Monitoring Technology for Wheat Stripe Rust, Journal of Northwest Sci-Tech University of Agriculture and Forestry (Natural Sciences Edition), Aug. 2005, vol. 33, China Academic Journal Electronic Publishing House.
Xianlin Yang, Detection of Anisakid Larvae in Marine Fish Fillets by Imaging Technique, China Excellent Doctoral and Master Thesis Full Text Database (Master) Engineering Science and Technology Series 1, Mar. 15, 2014.
Jens Petter Wold et al., Detection of Parasites in Cod Fillets by Using SIMCA Classification in Multispectral Images in the Visible and NIR Region, Applied Spectroscopy, 2001, pp. 1025-1034, vol. 55, No. 8.

* cited by examiner

INTELLIGENT RECOGNITION METHOD OF HYPERSPECTRAL IMAGE OF PARASITES IN RAW FISH

CROSS REFERENCE TO RELATED APPLICATIONS

The present application claims the benefit of Chinese Patent Application No. 202210263992.1 filed on Mar. 17, 2022, the contents of which are incorporated herein by reference in their entirety.

FIELD

The subject matter herein generally relates to optical detection technology, and particularly to an intelligent recognition method of hyperspectral image of parasites in raw fish.

BACKGROUND

A Chinese patent application of CN 201980030718.6 discloses a method and a system for the identification, and optionally the quantitation of, discrete objects of biological origin such as cells, cytoplasmic structures, parasites, parasite ova, and the like which are typically the subject of microscopic analysis. The patent application may be embodied in the form of a method for training a computer to identify a target biological material in a sample. The method may include accessing a plurality of training images, the training images being obtained by light microscopy of one or more samples containing a target biological material and optionally a non-target biological material. The training images are cropped by a human or a computer to produce cropped images, each of which shows predominantly the target biological material. A human then identifies the target biological material in each of the cropped images where identification is possible, and associating an identification label with each of the cropped images where identification was possible. A computer-implemented feature extraction method is then applied to each labeled cropped image. A computer-implemented learning method is then applied to each labeled cropped image to associate extracted features of a biological material with a target biological material.

Specific to the identification of worm eggs in fish fillets, the above methods have the following problems:

Referring to FIG. 1, in FIG. 1, the color of the worm eggs and the edge of the fish fillet is relatively difficult to distinguish; referring to FIG. 2, FIG. 2 illustrates the raw average spectral signals of different objects in the raw fish area, and the spectral signals in FIG. 2 are difficult to distinguish, thus, the worms cannot be distinguished.

The technical problem to be solved in the present disclosure is that how to accurately distinguish the parasite body in the fish fillets.

SUMMARY

A purpose of the present disclosure is to provide an intelligent recognition method of hyperspectral image of parasites in raw fish. The intelligent recognition method of hyperspectral image of parasites in raw fish includes:

step 1: obtaining a hyperspectral image of the raw fish in a wavelength range from 300 to 1100 nm;

step 2: extracting a grayscale image of the hyperspectral image at a wavelength value of 437 nm, and obtaining a position range of fish meat in the grayscale image by performing a median filtering process and a binarization process on the grayscale image;

step 3: extracting spectral signals of pixel points in the position range of the hyperspectral image, performing a first-order derivative process on the spectral signals, and import the spectral signals after the first-order derivative process into a preset first model, a second model, and a third model for analysis;

the first model analyzing average spectral signals of first-order derivative in a wavelength range of 484.88 to 655.95 nm, for characterizing parasite bodies, an edge of the fish meat, and the fish meat;

the second model analyzing average spectral signals of first-order derivative in a wavelength range of 368.37 to 461.18 nm, for characterizing the parasite bodies and the fish meat;

the third model analyzing average spectral signals of first-order derivative in a wavelength range of 892.64 to 1002.86 nm, for characterizing the parasite bodies and the edge of the fish meat; and recognizing whether there is any parasite in the raw fish by using the first model, the second model, and the third model.

In the intelligent recognition method of hyperspectral image of parasites in raw fish, there are M*N pixels in the hyperspectral image, and each pixel has spectral signals;

the step 2 includes: extracting a gray value of the spectral signals of each pixel at the wavelength value of 437 nm, combining the gray values of the spectral signals of M*N pixels at the wavelength value of 437 nm into a grayscale image, performing a median filtering process, a binarization process, and a black and white reversal on the grayscale image, and obtaining the position range of the fish meat in a black-and-white image.

In the intelligent recognition method of hyperspectral image of parasites in raw fish, training methods of the first model, the second model and the third model in the step 3 includes:

step 31: obtaining hyperspectral images of the raw fish for training in advance;

step 32: labeling and extracting pixel points of the fish meat, the parasite bodies, and the edge of the fish meat in the hyperspectral images;

step 33: importing average spectral signals of first-order derivative in the wavelength range of 484.88 to 655.95 nm of each pixel point obtained in the step 32 into the first model for training, importing average spectral signals of first-order derivative in the wavelength range of 368.37 to 461.18 nm of each pixel point obtained in the step 32 into the second model for training, and importing average spectral signals of first-order derivative in the wavelength range from 892.64 to 1002.86 nm of each pixel point obtained in the step 32 into the third model for training;

the average spectral signals of first-order derivative are a set of response values of a plurality of spectral signal curves after the first-order derivative at each wavelength.

In the intelligent recognition method of hyperspectral image of parasites in raw fish, performing a first-order derivative process on the spectral signals in the step 3 includes:

performing a Savitzky Golay (SG) smooth filtering and a standard normalized variate (SNV) correction process on the spectral signals, and performing the first-order derivative process on the spectral signals after the SG smooth filtering and the SNV correction process.

In the intelligent recognition method of hyperspectral image of parasites in raw fish, the step 3 further includes:

recognizing pixel points that belong to the parasite bodies by using the first model, the second model, and the third model, and obtaining a set of pixel points that represents the parasite bodies and positions of the pixel points that belong to the parasite bodies.

BRIEF DESCRIPTION OF THE DRAWINGS

In order to clearly explain technical solutions of embodiments of the present disclosure or in the related art, drawings used in the description of the embodiments or the related art are briefly described below. Obviously, the drawings as described below are merely some embodiments of the present disclosure. Based on these drawings, other drawings can be obtained by those skilled in the art without paying creative efforts.

DETAILED DESCRIPTION

Figure 1:
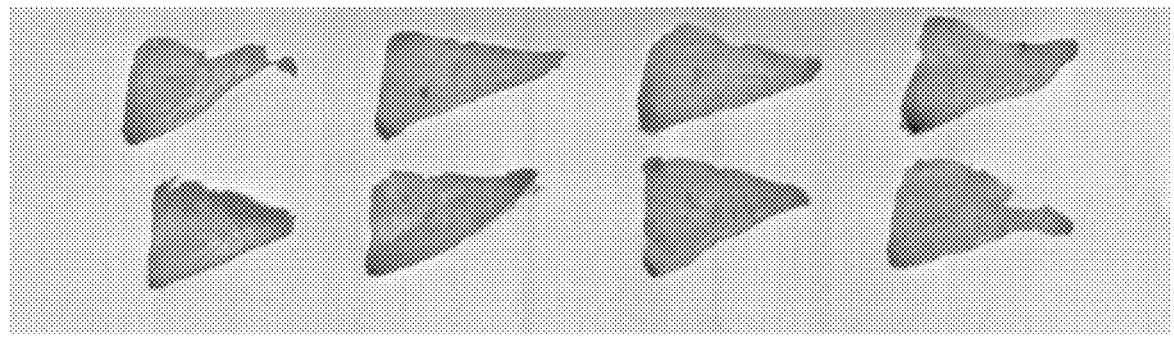
FIG. 1 illustrates an image of raw fish according to the present disclosure.

Multiple embodiments are described in the present disclosure, but the description is exemplary rather than limiting, and there may be more embodiments and implementation solutions within the scope of the embodiments described in the present disclosure. Although many possible combinations of features are shown in the drawings and discussed in the detailed description, many other combinations of the disclosed features are also possible. Unless specifically limited, any feature or element of any embodiment may be used in combination with or in place of any other feature or element of any other embodiment.

When describing representative embodiments, the specification may have presented methods and/or processes as a specific sequence of steps. However, to the extent that the method or process does not depend on the specific order of steps described in the present disclosure, the method or process should not be limited to the specific order of steps described. As understood by those of ordinary skills in the art, other orders of steps are also possible. Therefore, the specific order of steps set forth in the specification should not be interpreted as limitation to the claims. In addition, the claims for the method and/or process should not be limited to the steps performed in the written order, and those of skilled in the art may readily understand that these orders may vary and still remain within the essence and scope of the embodiments of the present disclosure.

Unless otherwise defined, technical terms or scientific terms used in the embodiments shall have common meanings as construed by those of ordinary skills in the art to which the present disclosure pertains. The words "first", "second" and the like used in the embodiments of the present disclosure do not represent any order, quantity or importance, but are merely used to distinguish among different components. The words "include", "contain" or the like mean that elements or articles appearing before the words cover elements or articles listed after the words and their equivalents, without excluding other elements or articles. The words "connect", "link" or the like are not limited to physical or mechanical connection, but may include electrical connection, whether direct or indirect.

Embodiment 1

An intelligent recognition method of hyperspectral image of parasites in raw fish is provided, the method includes the following steps:

Step 1: obtaining a hyperspectral image of the raw fish in a wavelength range of 300 to 1100 nm; there are M*N pixels in the hyperspectral image, and each pixel has spectral signals.

Figure 2:
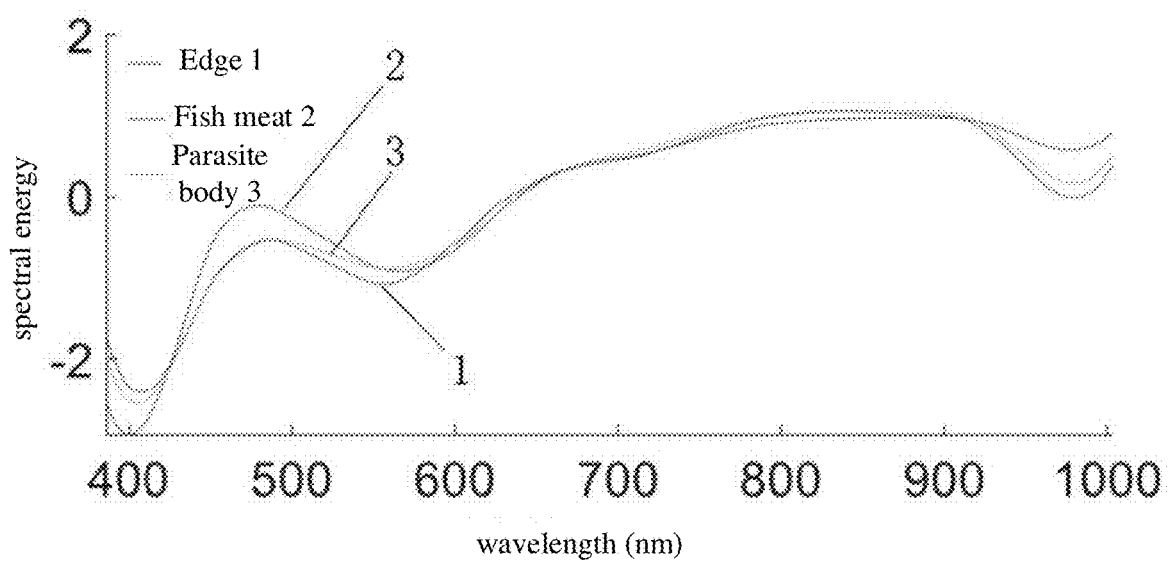
FIG. 2 is a schematic view of spectral signals of a hyperspectral image in FIG. 1 according to the present disclosure.

The hyperspectral image is shown in FIG. 2, it is difficult to separate the parasite body, the edge of the fish meat, and the fish meat, although the three types of meat can be distinguished at about a wavelength of 400 nm and a wavelength of 980 nm in FIG. 2, with the drift of the interference noise signal such as fillet thickness and the angle of the light source, the fish fillets under different conditions will generate more obvious differences.

Step 2: extracting a grayscale image of the hyperspectral image at any wavelength value in the wavelength range of 437 to 446 nm; obtaining a position range of the fish meat in the grayscale image by performing a median filtering process and a binarization process on the grayscale image.

Figure 3:
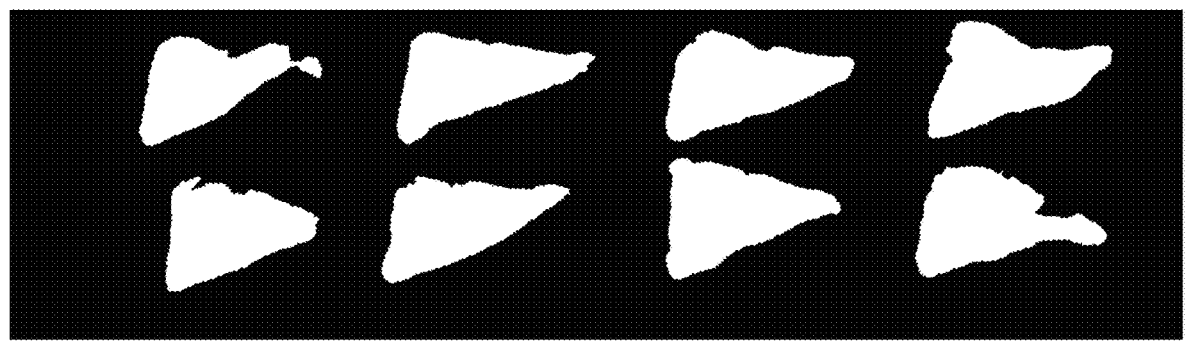
FIG. 3 illustrates a black-and-white image after a greyscale process on FIG. 1 according to the present disclosure.

In detail, extracting a grayscale image of the hyperspectral image at any wavelength value in the wavelength range from 437 nm to 446 nm includes: extracting a gray value of spectral signals of each pixel point at a wavelength of 437 nm, and combining the gray values of the spectral signals of M*N pixels at the wavelength of 437 nm into the grayscale image. Obtaining a position range of the fish meat in the grayscale image by performing a median filtering process and a binarization process on the grayscale image includes: performing the median filtering process, the binarization process, and a black and white reversal on the grayscale image, and obtaining the position range of the fish meat in the black-and-white image, which is shown in FIG. 3.

Figure 5:
FIG. 5 is a schematic view of processing a grayscale image by using a median filter algorithm.

The median filtering can effectively remove the noise points that may exist in the image according to a feature of small difference of pixel values in a small area of the image. Referring to FIG. 5, a filter window with a size of 3×3 is utilized in the present disclosure. The pixel values in the middle of the window are replaced with an average value of all pixels in the window. The window is moved from left to right and from top to bottom on the image by one pixel at a time.

The binarization process is to convert the grayscale image (the pixel values range from 0 to 255) into a black-and-white image (the grayscale value of pure black is 0 and the grayscale value of pure white is 1), which helps to locate the target in the image. In one embodiment, a binarization threshold is 0.8, that is, the grayscale values that are greater than 255*0.8=127.5 become pure white 1, the grayscale values that are less than or equal to 127.5 become pure black 0.

Extracting the grayscale image of the hyperspectral image at any wavelength value in the wavelength range from 437 to 446 nm is an important innovation in the present disclosure. The wavelengths other than 437 to 446 nm have been tested, and the separation of the fish meat area (including the edge of the fish meat) and the background cannot be achieved. In the embodiment, referring to FIG. 3, the fish meat range can be distinguished perfectly at the wavelength of 437 nm.

Step 3: extracting the spectral signals of the pixel points in the position range in the hyperspectral image, performing a first-order derivative process on the spectral signals, and import the spectral signals after the first-order derivative process into a preset first model, a second model, and a third model for analysis.

As illustrated in FIG. 2, the spectral signals refer to a curve between spectral bands and spectral values, the abscissa of the curve is the wavelength, and the ordinate of the curve is the reflectance or the spectral energy.

The specific application of spectral signals can be found in "Journal of Northwest Agricultural University of Science and Technology (Natural Science Edition)", Vol. 23, 2005, with the theme "Research on Hyperspectral Remote Sensing Monitoring Technology of Wheat Stripe Rust", Cai Chengjing et al. FIGS. 1 to 4 describe the spectral signals in a certain band.

The first-order derivative of a single spectral response signal curve is calculated by a formula of (spectral energy value$_{X+1}$–spectral energy value$_X$)/(wavelength$_{X+1}$–wavelength$_X$), in the formula, X is a value of X-th point in the spectral signal curve.

The first model is used to analyze the average spectral signals of first-order derivative in the wavelength range of 484.88 to 655.95 nm, to characterize the parasite body, the edge of the fish meat, and the fish meat.

The second model is used to analyze the average spectral signals of first-order derivative in the wavelength range of 368.37 to 461.18 nm, to characterize the parasite body and fish meat.

The third model is used to analyze the average spectral signals of first-order derivative in the wavelength range of 892.64 to 1002.86 nm, to characterize the edge of the parasite body and fish meat.

If the first model, the second model, and the third model can recognize the features of the parasite body, it indicates that there are parasites in the raw fish, at the same time, obtaining a pixel point set represented by the parasite body and the position of the pixel points by recognizing the pixels that belong to the parasite body according to the first model, the second model, and the third model, and the positions of the pixels.

In one embodiment, the training methods of the first model, the second model and the third model in the step 3 include:

Step 31: obtaining hyperspectral images of the raw fish for training.

Step 32: labeling and extracting the pixel points of the fish meat, the parasite body, and the edge of the fish meat in the hyperspectral image.

Step 33: importing the average spectral signals of first-order derivative in the wavelength range of 484.88 to 655.95 nm of each pixel point obtained in step 32 into the first model for training, and importing the average spectral signals of first-order derivative in the wavelength range of 368.37 to 461.18 nm of each pixel point obtained in step 32 into the second model for training, and importing the average spectral signals of first-order derivative in the wavelength range of 892.64 to 1002.86 nm of each pixel point obtained in step 32 into the third model for training.

The average spectral signals of first-order derivative is defined as: the average spectral signals of first-order derivative of a number of spectral response signal curves are average values of the corresponding response values of the first-order micro-curves of the number of spectral response signal curves.

The number of spectral response signal curves refer to the spectral response signal curves of a number pixels of the same object such as the parasite body; the first-order micro-curve is obtained by performing the first-order derivation on the spectral response signal curve, and the curve formed by the average values of the corresponding response values of the number of first-order micro-curves is the average spectral signals of first-order derivative.

Figure 4:
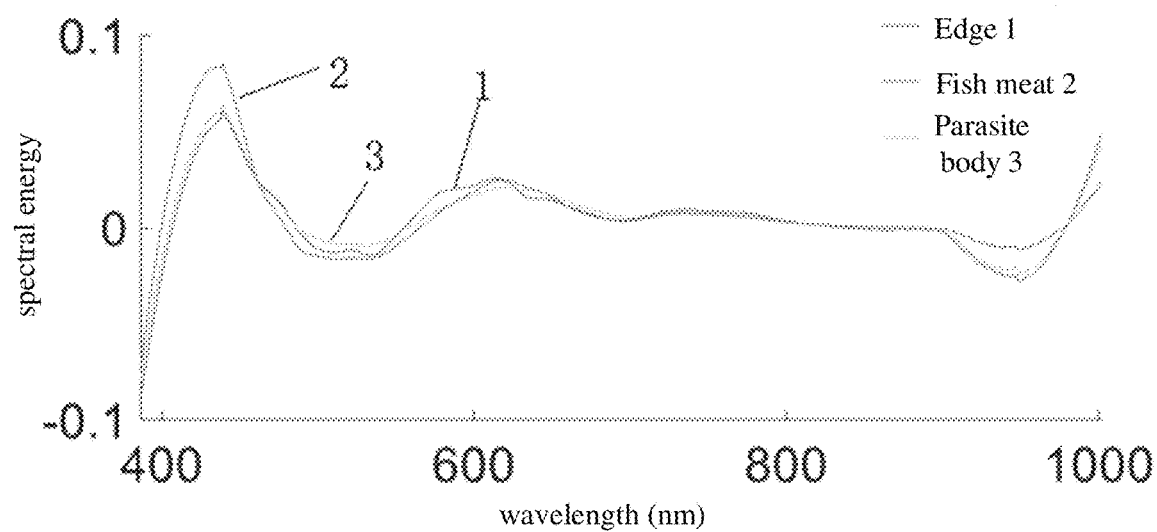
FIG. 4 is a schematic view of spectral signals after a first-order derivative process on the spectral signals of the hyperspectral image according to the present disclosure.

For example, in the first model, although the spectral signals in the wavelength range of 484.88 to 655.95 nm processed by the first-order derivative in FIG. 4 are not as distinct as the spectral signals in the wavelength ranges of 368.37 to 461.18 nm and 892.64 to 1002.86 nm, in the spectral signals of first-order derivative in the wavelength range of 484.88 to 655.95 nm, the curvature changes, the intersections, and the wave shapes of the curves represented by the three objects are different, the distinction contribution to the fish meat, the parasite body, and the edge is the largest.

The first model, the second model, and the third model are probabilistic neural networks (PNN). Steps 31 to 33 are repeated multiple times to obtain the first model, the second model, and the third model that are completed training.

The main classification model of the parasite body, the fish meat, and the edge is established by using a first-order derivative spectrum in the wavelength range of 484.88-655.95 nm, the recognition accuracy rate is 89.88%. The approved classification model of the parasite body and the fish meat is established by using the first-order derivative spectrum in the wavelength range of 368.37-461.18 nm, the recognition accuracy rate is 92.86%. The approved classification model of the parasite body and the edge of fish meat is established by using the first-order derivative spectrum in the wavelength range of 892.64-1002.86 nm, the recognition accuracy rate is 93.75%.

In conclusion, based on the above three models and the method in this embodiment, the recognition rate of parasite body in the raw fish can reach 95%.

Figure 6:
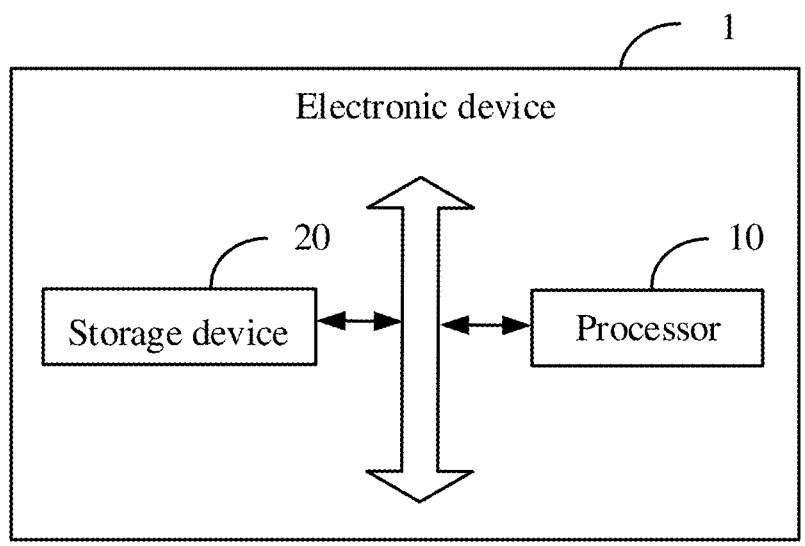
FIG. 6 is a block diagram of an embodiment of an electronic device according to the present disclosure.

FIG. 6 illustrates an electronic device 1 in one embodiment. The electronic device 1 includes, but is not limited to, a processor 10, a storage device 20, and a computer program. FIG. 6 illustrates only one example of the electronic device 1. Other examples can include more or fewer components than as illustrated or have a different configuration of the various components in other embodiments.

The processor 10 can be a central processing unit (CPU), a microprocessor, or other data processor chip that performs functions in the electronic device 1.

In one embodiment, the storage device 20 can include various types of non-transitory computer-readable storage mediums. For example, the storage device 20 can be an internal storage system, such as a flash memory, a random access memory (RAM) for the temporary storage of information, and/or a read-only memory (ROM) for permanent storage of information. The storage device 20 can also be an external storage system, such as a hard disk, a storage card, or a data storage medium.

The storage device 20 stores instructions, the processor 10 executes the computer program stored in the storage device 20 for implementing the intelligent recognition method of hyperspectral image of parasites in raw fish provided in the embodiments of the present disclosure. The computer program includes a recognition program, and further includes instructions.

Upon execution of the instructions stores in the storage device 20, the processor 10 is configured to: obtain a hyperspectral image of the raw fish in a wavelength range from 300 to 1100 nm;

extract a grayscale image of the hyperspectral image at a wavelength value of 437 nm, and obtain a position range of fish meat in the grayscale image by performing a median filtering process and a binarization process on the grayscale image;

extract spectral signals of pixel points in the position range of the hyperspectral image, perform a first-order derivative process on the spectral signals, and import the spectral signals after the first-order derivative process into a preset first model, a second model, and a third model for analysis.

Compared with prior art, the present disclosure selects a wavelength in the range of 437 to 446 nm for processing the hyperspectral image, which can accurately distinguish the fish meat and the background, locates the position of the fish meat, and then based on established model, imports the average spectral signals of first-order derivative in the wavelength range of 484.88 to 655.95 nm, 368.37 to 461.18 nm, 892.64 to 1002.86 nm into the corresponding models for analysis, respectively, the parasite bodies, the edge of the fish meat are characterized, the parasite bodies, and the fish meat are characterized, the parasite bodies and the edge of the fish meat are characterized through three models, respectively, a result that whether there is any parasite body in the fish meat can be obtained through the calculation results of the three model, compared with applying a main model and a first model analysis, the accuracy is significantly higher.

Technical features in the above embodiments can be combined arbitrarily. For concise description, not all possible combinations of the technical features in the above embodiments are described. However, any combination of the technical features described in the above embodiments should fall within the scope of the present disclosure, as long as no conflict occurs between the combined technical features.

The above embodiments, which are described in detail, are merely some implementations of the present disclosure, but they should not be construed to limit the scope of the present disclosure. It should be pointed out that, various modifications and improvements can be made by those skilled in the art without departing from the concept of the present disclosure. These modifications and improvements shall be encompassed by the protection scope of the present disclosure as defined by the appended claims.

What is claimed is:

1. An intelligent recognition method of hyperspectral image of parasites in raw fish comprising:
   step 1: obtaining a hyperspectral image of the raw fish in a wavelength range from 300 to 1100 nm;
   step 2: extracting a grayscale image of the hyperspectral image at a wavelength value of 437 nm, and obtaining a position range of fish meat in the grayscale image by performing a median filtering process and a binarization process on the grayscale image;
   step 3: extracting spectral signals of pixel points in the position range of the hyperspectral image, performing a first-order derivative process on the spectral signals, and import the spectral signals after the first-order derivative process into a preset first model, a second model, and a third model for analysis;
   the first model analyzing average spectral signals of first-order derivative in a wavelength range of 484.88 to 655.95 nm, for characterizing parasite bodies, an edge of the fish meat, and the fish meat;
   the second model analyzing average spectral signals of first-order derivative in a wavelength range of 368.37 to 461.18 nm, for characterizing the parasite bodies and the fish meat;
   the third model analyzing average spectral signals of first-order derivative in a wavelength range of 892.64 to 1002.86 nm, for characterizing the parasite bodies and the edge of the fish meat; and
   recognizing whether there is any parasite in the raw fish by using the first model, the second model, and the third model.

2. The intelligent recognition method of hyperspectral image of parasites in raw fish according to claim 1, wherein there are M*N pixels in the hyperspectral image, and each pixel has spectral signals;
   the step 2 comprises: extracting a gray value of the spectral signals of each pixel at the wavelength value of 437 nm, combining the gray values of the spectral signals of M*N pixels at the wavelength value of 437 nm into a grayscale image, performing a median filtering process, a binarization process, and a black and white reversal on the grayscale image, and obtaining the position range of the fish meat in a black-and-white image.

3. The intelligent recognition method of hyperspectral image of parasites in raw fish according to claim 1, wherein training methods of the first model, the second model and the third model in the step 3 comprises:
   step 31: obtaining hyperspectral images of the raw fish for training in advance;
   step 32: labeling and extracting pixel points of the fish meat, the parasite bodies, and the edge of the fish meat in the hyperspectral images;
   step 33: importing average spectral signals of first-order derivative in the wavelength range of 484.88 to 655.95 nm of each pixel point obtained in the step 32 into the first model for training, importing average spectral signals of first-order derivative in the wavelength range of 368.37 to 461.18 nm of each pixel point obtained in the step 32 into the second model for training, and importing average spectral signals of first-order derivative in the wavelength range from 892.64 to 1002.86 nm of each pixel point obtained in the step 32 into the third model for training;
   wherein the average spectral signals of first-order derivative are a set of response values of a plurality of spectral signal curves after the first-order derivative at each wavelength.

4. The intelligent recognition method of hyperspectral image of parasites in raw fish according to claim 1, wherein performing a first-order derivative process on the spectral signals in the step 3 comprises:
   performing a Savitzky Golay (SG) smooth filtering and a standard normalized variate (SNV) correction process on the spectral signals, and performing the first-order derivative process on the spectral signals after the SG smooth filtering and the SNV correction process.

5. The intelligent recognition method of hyperspectral image of parasites in raw fish according to claim 1, wherein the step 3 further comprises:
   recognizing pixel points that belong to the parasite bodies by using the first model, the second model, and the third model; and obtaining a set of pixel points that represents the parasite bodies and positions of the pixel points that belong to the parasite bodies.

\* \* \* \* \*